United States Patent
Cavallo (10) Patent No.: US 10,650,693 B2
(45) Date of Patent: May 12, 2020

(54) THERAPEUTIC MAT

(71) Applicant: Brain ABC's, Inc., Villa Park, IL (US)

(72) Inventor: Pam A. Cavallo, Villa Park, IL (US)

(73) Assignee: BRAIN ABC's, INC., Villa Park, IL (US)

( * ) Notice: Subject to any disclaimer, the term of this patent is extended or adjusted under 35 U.S.C. 154(b) by 161 days.

(21) Appl. No.: 15/366,915

(22) Filed: Dec. 1, 2016

(65) Prior Publication Data

US 2018/0158349 A1   Jun. 7, 2018

(51) Int. Cl.
| | |
|---|---|
| *G09B 5/06* | (2006.01) |
| *G16H 20/30* | (2018.01) |
| *G09B 19/00* | (2006.01) |
| *G09B 19/04* | (2006.01) |
| *A63B 22/00* | (2006.01) |

(52) U.S. Cl.
CPC .............. *G09B 5/06* (2013.01); *G09B 19/00* (2013.01); *G09B 19/003* (2013.01); *G09B 19/04* (2013.01); *G16H 20/30* (2018.01); *A63B 2022/0092* (2013.01); *A63B 2207/02* (2013.01)

(58) Field of Classification Search
USPC ........................................................ 434/185
See application file for complete search history.

(56) References Cited

U.S. PATENT DOCUMENTS

| | | | | |
|---|---|---|---|---|
| 3,024,020 A | * | 3/1962 | Alton ................. | A63B 69/0053 273/454 |
| 3,418,668 A | * | 12/1968 | Anderson .............. | A47K 3/002 4/583 |
| 4,645,458 A | * | 2/1987 | Williams ........... | A63B 69/0053 273/446 |
| 4,702,475 A | * | 10/1987 | Elstein ............... | A63B 69/0053 273/445 |
| 4,927,139 A | * | 5/1990 | Taltre ............... | A63B 21/00047 482/142 |
| 5,469,740 A | * | 11/1995 | French ................. | A61B 5/1036 273/445 |
| D365,152 S | * | 12/1995 | Park ............................ | D24/212 |
| 5,839,976 A | | 11/1998 | Darr | |
| 5,913,727 A | * | 6/1999 | Ahdoot ................... | A63F 13/06 345/156 |
| 5,997,304 A | * | 12/1999 | Wood ..................... | G09B 5/062 434/156 |
| 6,143,946 A | * | 11/2000 | Docter ................ | A61F 13/0269 602/41 |
| 7,018,267 B2 | * | 3/2006 | Delaney ................. | A63H 18/00 135/125 |

(Continued)

OTHER PUBLICATIONS

International Patent Application No. PCT/US2017/061761; Cavallo, Therapeutic Mat; Filing date Nov. 15, 2017.

(Continued)

*Primary Examiner* — John E Simms, Jr.
*Assistant Examiner* — Dolores R Collins
(74) *Attorney, Agent, or Firm* — Michael P. Mazza, LLC (57) ABSTRACT

A therapeutic tool, and method for using it, for integrating motor, sensory and cognitive skills and progressively developing coordination and cognitive functioning. In a preferred embodiment, a mat is provided with colored shapes forming a figure-8 path. The shapes may be colored differently to progress along the figure-8 path. The shapes may be lights, and a computer may be used to program the lights, or provide music, to prompt the user to progress along the figure-8 path.

8 Claims, 6 Drawing Sheets

(56) References Cited

U.S. PATENT DOCUMENTS

| | | | |
|---|---|---|---|
| 7,115,071 B1 | 10/2006 | Sunbeck | |
| 7,645,219 B1* | 1/2010 | Buth | A61H 1/0237 |
| | | | 482/121 |
| 7,708,676 B2 | 5/2010 | Sunbeck | |
| 7,761,936 B2* | 7/2010 | White | A47G 27/0225 |
| | | | 4/581 |
| 9,111,516 B1* | 8/2015 | Saraceni | G10H 1/34 |
| 2004/0197419 A1* | 10/2004 | Cole | A61K 45/06 |
| | | | 424/617 |
| 2005/0233862 A1 | 10/2005 | Madigan | |
| 2009/0043170 A1 | 2/2009 | Sulkin | |
| 2009/0241978 A1* | 10/2009 | Moretti | A47K 7/026 |
| | | | 132/200 |
| 2010/0187213 A1* | 7/2010 | Cheatham, II | A61F 7/007 |
| | | | 219/202 |
| 2011/0296704 A1* | 12/2011 | Jefferson | F26B 5/16 |
| | | | 34/90 |
| 2013/0181907 A1* | 7/2013 | Russell | G06F 3/0219 |
| | | | 345/172 |
| 2013/0273305 A1* | 10/2013 | Rodd | A47G 27/0243 |
| | | | 428/99 |
| 2016/0007787 A1* | 1/2016 | Johnson | A47G 27/0231 |
| | | | 428/58 |
| 2016/0166876 A1* | 6/2016 | Goh | G06F 19/00 |
| | | | 482/9 |
| 2018/0207052 A1* | 7/2018 | Gallagher | A61H 7/001 |

OTHER PUBLICATIONS

Sunbeck, Deborah, Infinity Walk: Preparing your mind to learn! (1996), Jalmar Press, Torrance, CA. ISBN 1-880396-31-9.

Sunbeck, Deborah, The Complete Infinity Walk, Book 1: The Physical Self. (2002), The Leonardo Foundation Press, ISBN 0-9705164-6-0.

"Infinity Walk—A Cutting-Edge Tool in Brain Injury Rehabilitation." Northeast Center for Special care website. 2007 Retrieved Nov. 6, 2011.

Kawar, Mary, "Oculomotor Control: An Integral Part of Sensory Integration." (2002), In Anita C. Bundy, Shelly J. Lane, Elizabeth A. Murray. Sensory Integration: theory and Practice (2 ed.). Philadelphia: F.A. Davis Commpany. pp. 353-357. ISBN 0-8036-0545-5.

https://www.revolvy.com/main/index.php?s=Infinity%20Walk.

https://www.youtube.com/watch?v=pjKQeVFJVyk.

http://guruaam.com/1/post/2015/08/8-shaped-walk-maintain-good-health.html.

http://www.fairview.org/healthlibrary/Article/84837.

http://www.thebestbrainpossible.com/quick-tips-for-a-better-brain/.

Marina, Ann, Preserve Your Brain: Tools for Growing Mental Fitness.

Blog: Play-Doh in Your Head.

Brandt, A.C, Atwood, P.E., Farrington, W.J., Van, J., Lowry, K.A.; The figure-of-8 walk test: A clinical measure of motor skill in walking for persons wit Parkinson's Disease [abstract]. Movement Disorders 2015;30 Suppl 1:677 The Figure-of-8 Walk Test: A Clinical Measure of Motor Skill in Walking for Persons With Parkinson's Disease.

htttps://www.youtube.com/watch?v=pjKQeVFJVvk.

https://www.youtube.com/watch?v=in_WnGqkiQE.

https://www.youtube.com/watch?v=FRWMRZ_64co.

https://www.youtube.com/watch?v=Y5jAGZ8SWJA.

https://www.youtube.com/watch?v=v4Z5dNQ_0Hw.

https://www.youtube.com/watch?v=GrYNUKybkuc.

* cited by examiner

THERAPEUTIC MAT

BACKGROUND OF THE INVENTION

The present invention generally relates to an interactive mat for enhancing the cognitive skills of individuals.

Benefits of walking in a Figure-8 or "Infinity Walking" are known. Infinity Walk® is a therapeutic method for progressively developing coordination and certain areas of cognitive functioning. It is typically used with compromised individuals such as those with brain injuries or learning disabilities. Teachers and therapists use it to improve some of the essential foundation skills that must be mastered before learning can occur.

A beginning student or patient learns to walk smoothly in a figure-eight pattern while looking at an object or person across the room. As they become able to do that consistently, other physical and mental activities are added to the coordinated walking. An advanced walker can maintain a smooth figure-eight walk while doing several other activities, e.g., simultaneously gesturing and doing mental arithmetic as they converse with their teacher or therapist.

Infinity Walking can be done under a variety of conditions: indoors or outdoors, on foot or when riding a wheelchair, therapeutic riding horse, or other means of seated ambulation. There are systems of curved handrails that facilitate Infinity Walking by those unable to stand or walk on their own.

Developed in the 1980s by clinical psychologist Deborah Sunbeck, the Infinity Walk® is based on studies of cognitive science, neuropsychology, and practical applications of EEG research on lateralized readiness potential. It strives to improve the sensorimotor functioning of those who practice it. In developing the method, Dr. Sunbeck also applied knowledge of social facilitation and intrinsic motivation to the task of creating a self-motivating method of physical and mental skill-building that would help the user develop resilient self-regulated learning strategies for future challenges.

Infinity Walk® is used in fields including elementary education, special education, physical therapy and occupational therapy. It has been used by U.S. physical and occupational therapists in the rehabilitation of persons with brain injuries. It has been recognized as a particularly effective activity in developing multisensory integration in occupational therapy, including some clients with learning disabilities. In a 1993 study, learning disabled elementary school students who completed an Infinity Walk® program showed significant improvement in reading readiness, word identification, word comprehension, and reading passage comprehension. See https://en.wikipedia.org/wiki/Infinity Walk Dr. Sunbeck claims that the walker should look at a fixed point while walking in a FIGURE-8. However, the walker must work up to the skill level of being able to multi-task the movements required to infinity walk, while also looking at a fixed point while walking. The present invention was created to facilitate such multi-tasking skills.

Dr. Sunbeck obtained two patents on her Infinity Walkabout® handrail system, U.S. Pat. Nos. 7,708,676 and 7,115,071.

Infinity Walk® (a registered trademark of Dr. Sunbeck) is a promising method for accelerating learning and performance for many adults and children. Infinity Walk® is a fun, self-paced, and intrinsically rewarding program that trains and prepares individuals for successful action in life, academics, and career.

The method is both very simple and quite profound. This paradox comes from the foundation of the method being anchored to a seemingly simple repetitive movement: walking in a figure-eight pattern. The systematic refinement of this movement and the careful timing of additional multitasking skills to the basic movement enables the potential for profound change in the Infinity Walker. The unique way in which the figure-eight movement pattern is progressively combined with sensory, perceptual, language, cognitive and relational skills can produce positive change in the whole person, on every level of growth. The Infinity Walk® theory and method are applicable to all models of learning: developmental, remedial and accelerated/gifted learning.

Infinity Walkers don't need to "walk" to benefit from the method. Infinity Walk® practice can be assisted by the use of children's strollers, wheelchairs, and therapeutic riding horses. For those needing some walking assistance, the Infinity WalkAbout® handrail system offers adjustable height and width, single or double assistive railing for practice of Infinity Walking. This also allows older seniors to benefit from natural daily ambulation, and the Infinity Walk® method, with support close-by throughout the figure-eight track.

Additional benefits can be gained by adding "Infinity Swimming" to aquatic exercise programs and "Infinity Crawling" to children's play.

SUMMARY OF THE INVENTION

The objects mentioned above, as well as other objects, are solved by the present invention, which overcomes disadvantages of prior FIGURE 8-inducing tools, while providing new advantages not previously associated with them.

In a preferred embodiment, a therapeutic tool is provided for integrating motor, sensory and cognitive skills, and progressively developing coordination and cognitive functioning. The therapeutic tool includes a mat designed to be walked on and having an upper surface with a plurality of colored shapes collectively forming a figure-8 path. Preferably, at least some of the shapes are colored differently than at least others of the shapes, and the different colors prompt a user of the mat to progress along the figure-8 path.

In one particularly preferred embodiment, the shapes form circles, with each of the four legs of the figure-8 path being of a different color of circles. Alternatively, each leg of the figure-8 path may include a different shape and/or a different color. For example, a first leg of the figure-8 path may have circular shapes, and a second leg of the figure-8 path may have triangular shapes. The same or different colors for each leg may be employed.

In another particularly preferred embodiment, at least some of the shapes may be lights (e.g., LEDs), and a (e.g.,) programmable computer with a controller and an electronic memory (e.g., an iPad®, an iPhone® or other computer) may be electronically connected to the mat, enabling the programming of the lights so that the lights may be turned on and off in predetermined sequences designed to prompt a user of the mat to progress along the figure-8 path. Preferably, the computer can save progress of individual users on the mat, and play a particular program, including light sequencing or music or both, targeted to individual users.

Use of the mat enables users to make substantial gains in one or more of the following areas: attention to task behavior; midline and bilateral play skills; articulation; use of expressive language; ambulatory skills; sensory integration skills; and attention-to-task behavior.

A method for using a therapeutic tool for integrating motor, sensory and cognitive skills and progressively developing coordination and cognitive functioning, is also provided. A mat is provided having an upper surface with a plurality of colored shapes collectively forming a figure-8 path with four different legs; preferably, at least some of the shapes are colored differently than at least others of the shapes. Each leg of the figure-8 path may include shapes with different colors, thereby prompting a user of the mat to progress along the figure-8 path.

In one preferred method, at least some of the shapes include programmable lights. A computer may be electronically connected to the mat, enabling the programming of the lights so that the lights may be turned on and off in predetermined sequences designed to prompt a user of the mat to progress along the figure-8 path. Use of the tool enables users to make substantial gains in one or more of the following areas: attention to task behavior; midline and bilateral play skills; articulation; use of expressive language; ambulatory skills; sensory integration skills; and attention-to-task behavior.

Definition of Claim Terms

The terms used in the claims are intended to have their broadest meaning consistent with the requirements of law. Where alternative meanings are possible, the broadest meaning is intended. All words used in the claims are intended to be used in the normal, customary usage of grammar and the English language.

BRIEF DESCRIPTION OF THE DRAWINGS

The novel features which are characteristic of the invention are set forth in the appended claims. The invention itself, however, together with further objects and attendant advantages thereof, can be better understood by reference to the following description taken in connection with the accompanying drawings, in which:

The components in the drawings are not necessarily to scale, emphasis instead being placed upon clearly illustrating the principles of the present invention. In the drawings, like reference numerals designate corresponding parts throughout the several views.

DETAILED DESCRIPTION OF THE PREFERRED EMBODIMENT

Set forth below is a description of what are believed to be the preferred embodiments and/or best examples of the invention claimed. Future and present alternatives and modifications to this preferred embodiment are contemplated. Any alternatives or modifications which make insubstantial changes in function, in purpose, in structure, or in result are intended to be covered by the claims of this patent.

The various forms of the interactive mat of the present invention disclosed here, which enables figure-8 walking and unique cognitive learning as described below, are individually and collectively known as the Neuromat™. In one preferred embodiment, the Neuromat™ is a therapeutic mat 10 which uses visual prompting through the use of differently-colored shapes (e.g., circles 15, triangles 17, octagons 18 and squares 10, per FIG. 3) that encourage the walker to change directions in order to complete the figure-8. In its preferred embodiment, the Neuromat™ is a self-contained, portable mat that makes it very easy for parents, teachers and therapists to use in virtually any environment.

Preferably, the Neuromat™ is a colorful, fun and easy way to facilitate walking in a figure-8 pattern. It offers parents, teachers and therapists a multi-sensory approach to teaching virtually any person at any age how to walk (forward/backward), crawl, hop, skip or jump in a simple figure 8 pattern. This tool encourages practice between therapy sessions. For years we have known that this type of motor movement helps the brain to create new neuro pathways and in turn make the brain more efficient. As one moves through the figure-8 pattern, the brain has to quickly send and receive sensory data from one hemisphere to the other.

The motor movement of walking in a figure-8 pattern is based on years of research involving neuropsychology, cognitive functioning and EEG research. (www.infinity-walk.org). This strategic method encourages the brain to integrate many functional skills at the same time, thus increasing its ability to multi-task. When the brain is able to process sensory information and turn those messages into appropriate motor actions, learning takes place. There are many different cognitive ability levels, but the ability to use the brain to the best of its ability, is a skill that must be developed, practiced and maintained.

Research confirms that the brain is a very powerful and pliable tool. When a new neuropathway is formed, it must be practiced in order to become a learned skill. This new skill must be practiced again and again and again. Having said that, it is when this new skill becomes difficult and you work through the difficulty, that real change occurs. Muscles react much the same way. A muscle gets stronger when fatigue sets in and the muscle is pushed to go further. Think of your brain as the most important muscle in your body.

Figure 1:
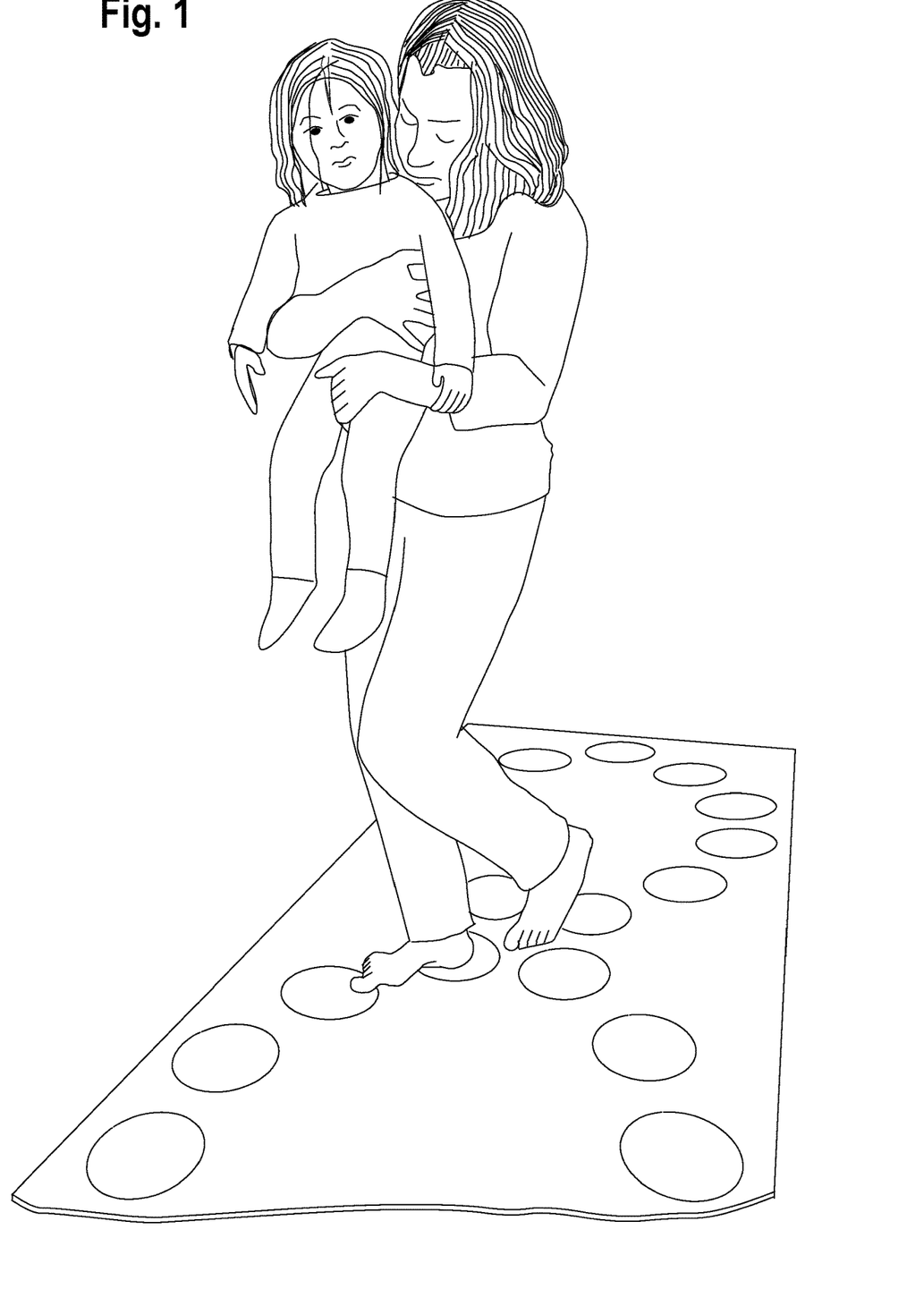
FIG. 1 is a perspective view of a preferred embodiment of the therapeutic mat of the present invention.
Figure 2:
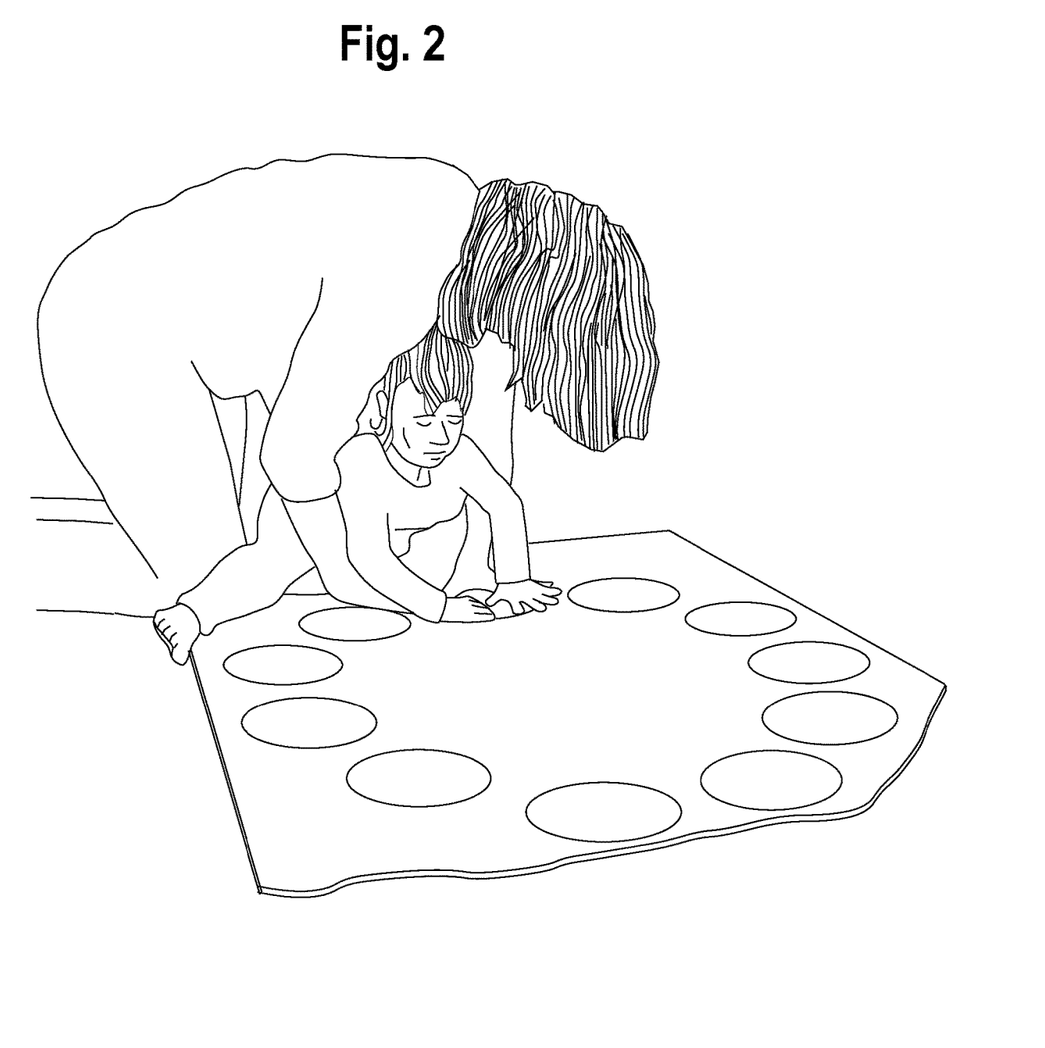
FIG. 2 is a partial perspective view similar to FIG. 1.

Referring now to FIG. 1, one preferred embodiment of the Neuromat™ generally referred to by reference numeral 10, is shown. Neuromat™ 10 may me made of deluxe yoga mat material, with a size, for example, of 36"×84". In one embodiment, colored circles 15 may be spray-painted on an upper surface 12 of the mat by hand with a paint that is safe for children. In this embodiment, the Neuromat™ is used as a tactile process with no computerized interface.

Figure 3:
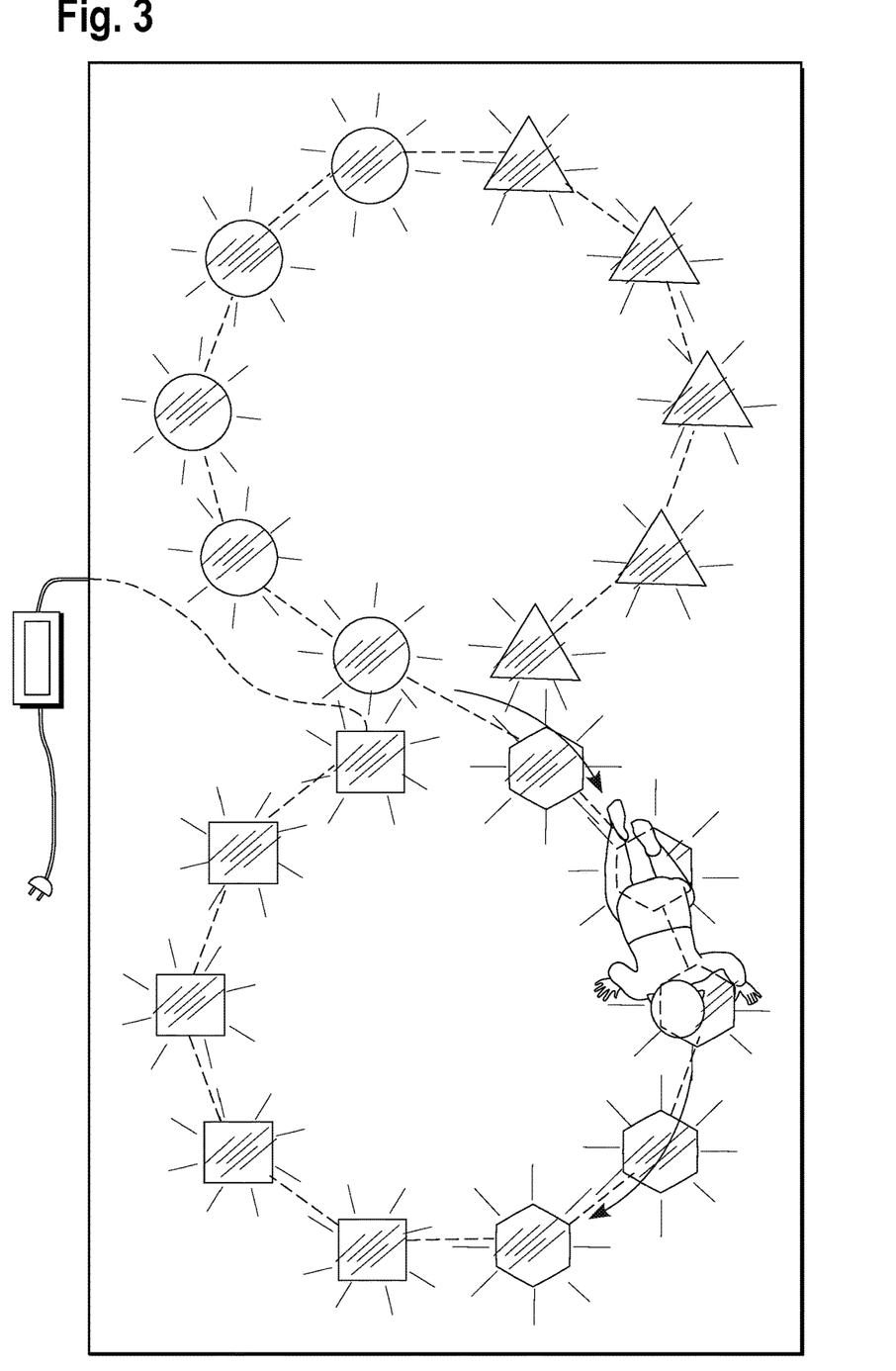
FIG. 3 is a perspective view of a different embodiment of a therapeutic mat.
Figure 4:
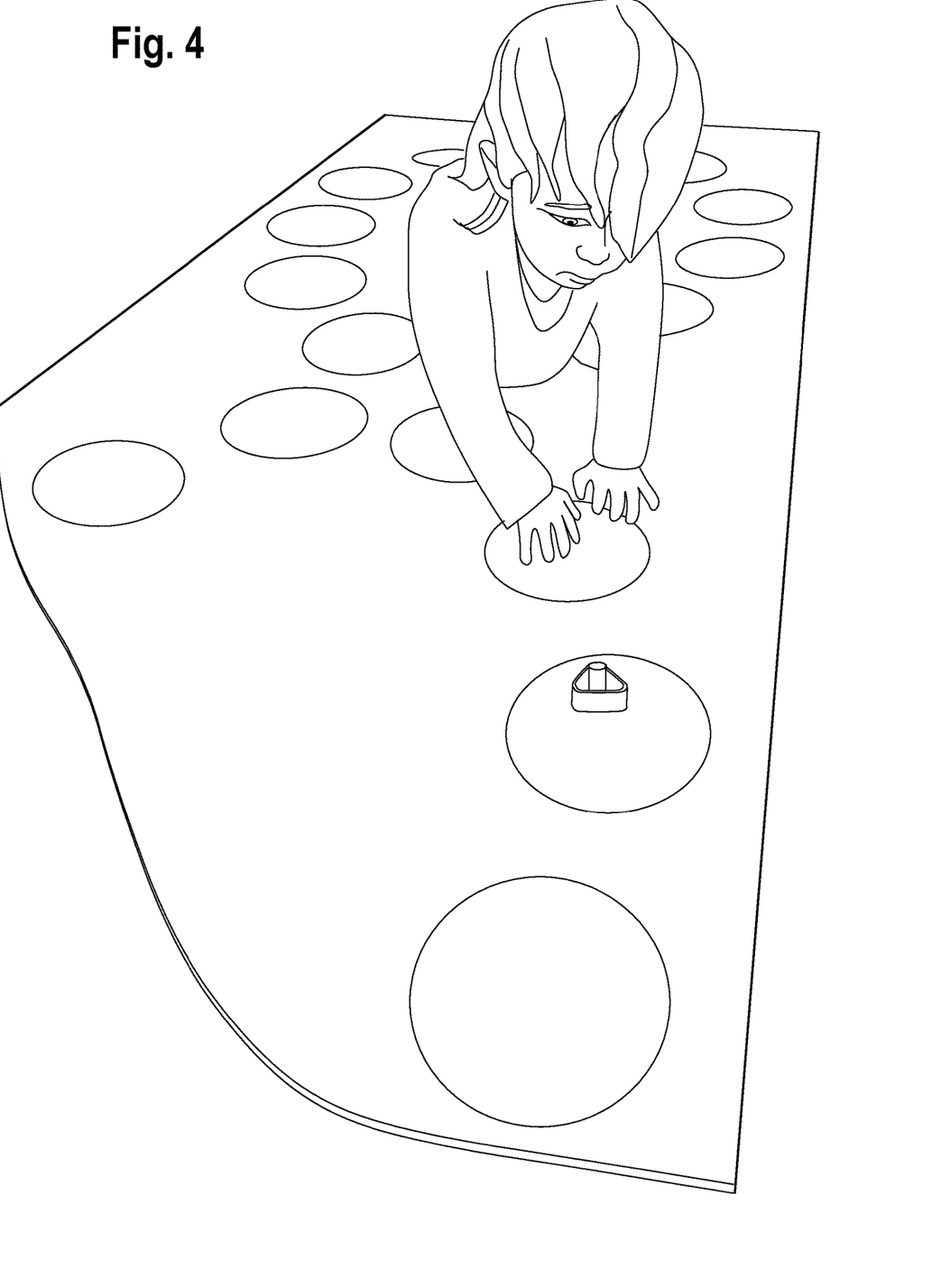
FIG. 4 is a partial perspective view similar to FIG. 2.
Figure 5:
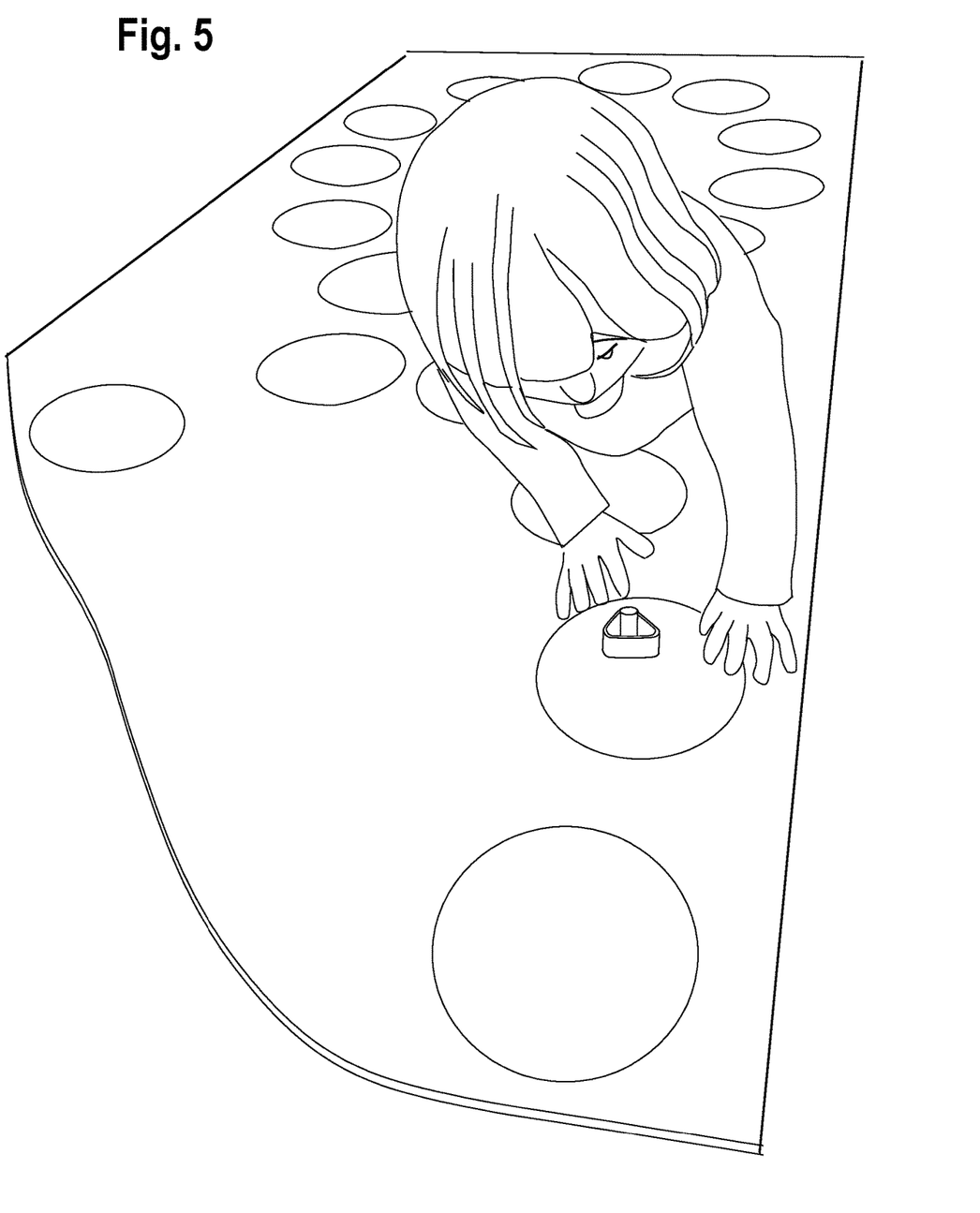
FIG. 5 is an enlarged partial perspective view similar to FIG. 5.
Figure 6:
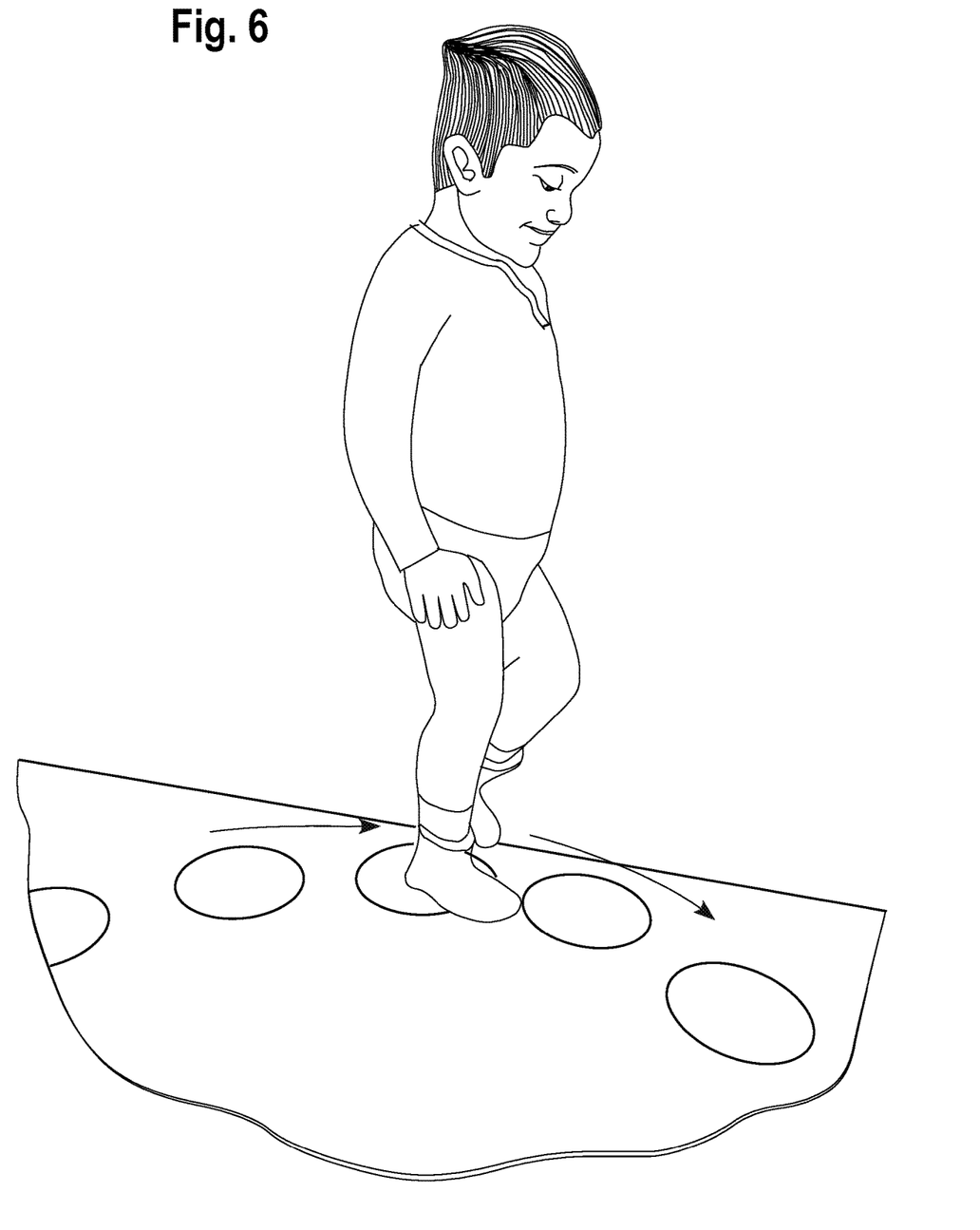
FIG. 6 is an enlarged partial perspective view similar to FIG. 2.

In another preferred embodiment, the Neuromat™ may be provided with colored circles that are lit by LEDs or other lighting. A general computer may interface with the mat, and the general computer may be programmed to light the circles in any patterns that are desired. Depending upon the activity desired, the lights may be strobed, act as marker lights, remain constantly lit, etc. As one non-limiting example, the lighting technology disclosed in U.S. Pat. No. 8,274,397, hereby incorporated by reference in its entirety, or an alternate technology, may be used to pre-program the general computer. Referring to FIGS. 3-5, computer 30 may be powered using cord 32 and may be connected to the Neuromat® using cord 34 or, alternatively, wirelessly. Alternatively, a program may be installed on an iPad®, iPhone® or other computer, for example, and then the programmable computer, for example, may be plugged into the Neuromat™ so that the lights on the Neuromat™ (such as LED light plug 24) may be programmed for on-and-off sequencing as desired. This will also allow the Neuromat™ to keep track of the progress of individual users, and allow the Neuromat™ to be programmed for an individual session for an individual user, so that users may incrementally learn on an individualized, pre-programmed basis.

The Neuromat™ helps to develop skills, including but not limited to:

- The brain's ability to multi-task
- Bilateral and midline movement
- Body-in-space awareness
- Motor planning
- Sensory awareness and integration
- Balance
- Motor Coordination
- Visual attention
- Pre-readiness learning skills (color identification, counting, one-to-one correspondence)
- Receptive and expressive language
- Attention The inventor, a special education teacher and developmental therapist, offers the following tips on using the Neuromat™. In order to receive the most benefit from the Neuromat™, the goal should be to do at least 4-5 rotations one way, then turn around and do the same number of rotations the other way. This should be done a few times during the day. The inventor suggests being creative and using the Neuromat™ in many different ways, such as:

- For infants and those not walking yet, encourage crawling along the figure-8 pattern. Lay toys out on the colored circles (every other color works nicely). Encourage crawling to a specific toy. Pick it up and put it in a bucket. Crawling stimulates the brain stem which promotes self-regulation. It works on shoulder stability, critical for fine motor activities. Hands, fingers and wrists become stronger, also critical for fine motor skills. Visual skills are reinforced by looking up and then back down again, thus encouraging the eyes to diverge and converge. This visual skill is important because as children begin to attend to books and learn to read, they must follow along word by word and line by line and not lose their place along the way. What many don't realize is that this skill is actually developed very early in life. Crawling also encourages right-left brain activity, balance, weight shifting, weight bearing on the joints, core strength, bilateral integration, body awareness and motor planning.
- Name each color as you crawl, step or touch it. This encourages one-to-one correspondence as well as learning the names of each color. Color recognition and counting using one-to-one correspondence are one of children's earliest introductions to reading and math.
- Try marching, jumping or hoping from one color to the next. This encourages motor planning, body in space awareness, visual attention, coordination and balance, midline and bilateral skills.
- Sing songs such as the ABC's as you move through the figure-8 pattern. Feel free to use a visual such as a sing-along-song on your phone, iPad or TV. This encourages expressive language (which is stimulated by motor movement), as well as visual attention, multi-tasking, attention to task.
- Dance and sing to music. Use rhyme and rhythm, get creative and have fun! Walk forward, backward, sideways, jump, hop, skip or crawl. Again, this encourages motor planning, body in space awareness, visual attention, coordination and balance, and midline and bilateral skills.
- Clap as you go. This encourages right-left brain activity, multi-tasking, bilateral and midline skills. I call it "layering of developmental domains."
- Color matching/stringing activity. Have the child lay a colored block to a matching colored circle. Once the blocks are matched up correctly, encourage the child to walk the figure-8, pick up a block and string it on a string, or simply stack the blocks in the middle of the figure-8. This encourages matching/sorting by color, one-to-one correspondence, increases hip/quad strength, fine motor development, eye-hand coordination, and visual attention as well as problem-solving skills.
- Push a car, truck or train in the figure-8. Add vocalizations such as "vrrrrmmm, choo-choo, beep-beep." Now you are layering cognitive domains! Again this realizes the great benefits of crawling, motor planning to push a toy, balance, coordination and multi-tasking as they vocalize all at the same time.
- Use chalk on the mat. Play connect-the-dots from one circle to the next. This encourages fine motor/pre-writing skills, visual attention, and problem-solving.
- Play games such as "Stop, Go". Sing "go,go,go,go" in any tune that appeals to you. Then say "Stop." Ask the child, "What color did you land on?" This encourages receptive language skills, color identification, and following directions.
- Play "Follow The Leader." Add singing to the fun and incidentally teach your child how to walk in a line as well as follow simple directions. (All preschool teachers love when children come to school and are able to walk in a line and follow simple directions!)
- Use the mat during story time. Direct the child to sit on a specific color. Learning how to sit and attend to a story is a learning skill that is underrated.

It should now be appreciated that the present invention has the following advantages. The Neuromat™ provides a consistent, efficient, measurable practice environment for which progress can be easily monitored and observed. The distance of the walk may be pre-programmed, and may be constant across users and environments. The Neuromat™ also offers an independent, mobile, physical, tactile, visual tool that facilitates the execution of walking in a figure-8 pattern. The visual prompt of each color change signals to the walker they must change direction. This enhances the completion of the movement without a disruption or confusion with directional changes as well as pace. This in turn provides consistent sensory and neuro feedback to the brain, thus increasing the overall benefits of walking in a figure-8 pattern.

The Neuromat™ is also an impromptu activity, such that there is virtually no prep time required, the mat may simply be unrolled, and hooked to a computer if present. Furthermore, there are no distractions or obstacles that interfere with the flow of the walking pattern.

The Neuromat™ provides material advantages over the traditional ways in which Infinity Walk® has been used. Additionally, Infinity Walk® experts have provided inconsistent and inefficient suggestions which may discourage instructors from using this therapeutic method. Such traditional methods and recommendations which may be problematic include:

- Walking around two chairs. The chairs are placed at each end of the invisible figure 8. Problems often occur as a chair suggests to the walker it is time to sit down. This can provide a huge distraction at each turn as the walker attempts to sit down and then must be physically and/or verbally redirected. This can greatly disrupt the flow of the learning pattern. The neurofeedback may be inconsistent and thus learning must start all over again. The walker may receive little or no visual imprint from walking the figure-8 pattern.

Two objects or toys placed on the floor for the walker to walk around, similar to the chairs mentioned above. Again, the figure-8 is invisible to the learner. The distraction here is of course the objects or toys. The walker may be visually distracted to pick up the object or toy, and do what they have been taught to do—interact with the object or toy. Again, learning may be inconsistent and again there may be no visual understanding of the figure-8 walking pattern.

Tape on floor. While this suggestion provides a visual cue for the walker, there are many problems with this approach. First, it takes time for the instructor to lay the tape on the floor in a figure-8 pattern, thus making it less efficient than the Neuromat.™ The shape of the figure-8 is often lopsided and most certainly is not consistent from one walker and/or walking session to the next. Also, the tape suggests to the walker they must walk "on the tape," which is only done in a precise heel-toe walking pattern. This walking pattern is often difficult for many walkers, so one of two things may occur. One, the walker concentrates on the heel-toe pattern, becomes frustrated and quits. Two, the pace of the walk is greatly reduced. The focus becomes more on staying on the tape as opposed to completing the figure-8 walking pattern.

Yarn or string as a substitute for the tape. The same disadvantages apply here as to the tape method; however, there are additional disadvantages with this approach. Most importantly, the yarn or string is not static, and tends to move as the walker steps on it, thus disrupting the flow of the walk. The walker must stop as the instructor readjusts the yarn or string.

Chalk on the floor. Again, a heel-toe pattern is visually suggested. Another disadvantage with chalk is that as the walker steps on the chalk, the chalk fades or disappears entirely.

One important aspect to remember is that the intention of walking in a figure-8, or Infinity Walk® pattern, is that it is to be completed without stopping, without hesitancy (no adjusting position/path) and completed with no changes in pace. The Neuromat™ is one tool that provides the walker with opportunities to become independent as the distance and visual cues and prompts are static and never change.

Supporting Advantages of the Neuromat™

The benefits of the Neuromat are always specific to each individual walker. The question is not whether the action of walking in a figure-8 pattern is effective, as research has already proven that. The question is, "Is the Neuromat™ more effective than other traditional figure-8 walking methods"? Each individual walker presents with different needs and therefore the results are individualized. Walking in a figure-8 pattern means many things to many different professionals. As a special education teacher and developmental therapist, the inventor became sensitized to the whole child. Furthermore, each walker presents with different needs and the results are based on observable behaviors.

The following are individual client results based on the use of the Neuromat™:

Client A:
Female; Age: 32 months
Needs: Born prematurely at 26 weeks. Diagnosed with decreased midline and bilateral motor skills, expressive speech delay, cognitive delay, visual-motor delay and social skill delay.
Activity: Neuromat™ used one time per week for six weeks at the beginning of each developmental therapy session at daycare.
Development: Initially, the client was not able to complete a figure-8 walking pattern. She was able to walk a straight line, but not able to motor plan turning the body and following a curved path. She required maximum physical assistance. Oct. 7, 2016, she started using Neuromat™ in the home on a daily basis as instructed. Following one week, results are as listed:
  Increased expressive as well as spontaneous language. Went from one word utterances to 3-5 word utterances
  Initially able to repeat only 1-word utterances and 2-word utterances were unintelligible. Now able to repeat at least 3-word utterances up to 5-word utterances with intelligible speech. ("I want more pizza please.")
  Improved articulation. Went from dropping final consonants sounds to intelligible consonant/vowel/consonant words. ("ball, yes, red, hat").
  Improved midline and bilateral skills. Progressed from inability to use both hands at the same time as well as in the midline of her body, to easily and spontaneously using both hands at the same time in order to orient puzzle pieces and complete simple puzzles.
  Improved visual-motor skills. Initially not able to look down at the colored circles, now able to maintain visual focus for 2-3 rotations without adult prompting. In addition, now able to visually scan entire vision field and match like items with one variable (color-coded word with picture of colored object).
  Increased attention to task behavior. Went from easily distractible and not able to attend to an activity for more than 2-3 minutes to attending to an activity for 10-15 minutes.
  Increased cognitive ability. Now able to answer simple comprehension questions by vocalizing and/or pointing, able to follow verbal two-step directions, identify common objects by function, use problem-solving skills in order to meet individual needs by answering yes/no questions and making choices out of a field of two or more."

Client B:
Male; Age: 34 months
Needs: Brain injured at birth. Diagnosed with gross motor delay (wears AFO's on both feet), fine motor delay, sensory integration disorder, expressive/receptive language delay, cognitive delay, self-help delay, as well as emotional and coping delays.
Activity: Neuromat™ used at the beginning of each developmental therapy session 2× per month for two consecutive months.
Development: Initially, the client was not able to follow the figure-8 pattern. He walked in an oval pattern, but was not able to motor plan to follow intersecting lines. Results using the Neuromat™ were noticed within 7-10 days of using the mat once every 2-3 days, and are as listed:
  Noticeable improvement with ability to walk in a figure-8 pattern on the mat. Went from maximum physical adult assistance to minimal adult prompting.
  Increased use of bilateral and midline play skills. Now using individual and spontaneous use of both hands at the same during play Improved transition from one activity to another with little to no disruptive behavior.

Improved articulation with more intelligible speech.

Client C:

Male; Age: 35 months

Needs: Qualified at 28 months for Early Intervention services based on receptive and expressive language delay, sensory integration disorder, emotional and coping delays, limited attention to task behavior and overall cognitive delay.

Activity: Neuromat™ used at the beginning of therapy sessions for 8 consecutive weeks, one time per week.

Development: Initially, despite maximum adult assistance, client was unable to complete one full rotation of walking in a figure-8 pattern. He fell to the ground, dizzy and refused to get up. Following eight consecutive weeks, beginning with crawling on the Neuromat™, the results are as follows:

Physical development: The client is now able to walk at least 4-5 rotations each way on the Neuromat™ with minimal adult assistance.

Increased expressive language skills: Client progressed from a vocabulary of approximately 30 known words to over 250 known words within 4 weeks of using the Neuromat™ one time per week.

Receptive language skills: Progressed from a 43% delay to less than a 30% delay, which is considered to be within a typical limit.

Improved sensory integration skills. Initially demonstrated impulsive and abusive behavior to others. He was routinely hitting his brother, mother, peers and daycare provider. He had several temper outbursts daily with inability to share, take turns or transition activities. Now he is able control his impulsivity in order to make choices, share toys and take turns with adults during therapy, as well as with siblings with minimal adult assistance.

Improved emotional and coping behavior as stated above. Went from inconsistently able to follow a verbal direction during therapy, to now able to follow one and two-step directions while maintaining emotional control of his feelings and emotional expression. Client is now able to cooperatively play with adults as well as with peers with minimal adult supervision. Tolerance of joint activity was less than one minutes and now is up to 10-15 minutes.

Improved attention to task behavior. Initially client was unable to sit and attend for longer than 2 minutes at a time. Two weeks ago, client demonstrated on-task behavior for 15-20 minutes of working puzzles, stinging beads and listening to a story.

Improved overall cognitive ability. To date, it is safe to say that the client's current cognitive skills demonstrated during therapy no longer present with a cognitive or thinking delay.

Client D

Female; Age: 36 months

Needs: Diagnosed with Down syndrome. Delays across all developmental domains secondary to diagnosis. Expressive language delay, cognitive delay with limited multi-tasking ability, fine motor delay, reduced midline and bilateral play skills, as well as social and emotional/coping delay.

Activity: Neuromat™ is used one time per week at the beginning of every therapy session. The mat has been used consistently for the past two months.

Development: Initially the client was not able to look down while she walked in a figure-8 pattern and only able to complete two rotations one way. After using the Neuromat™ as indicated above, the results are as follows:

Initially client needed maximum adult assistance to complete two rotations on the Neuromat™, she is now able to complete 4-5 rotations each way with minimal adult assistance. She currently demonstrates little to no motor planning difficulty at each turn.

Initially not able to look down at her feet while she walked. Now able to spontaneously look down, orient and turn her body at each curve as well as turn herself all the way around and reverse the direction of the walk with minimal adult assistance.

Initially the client was not able to hold a toy with both hands in the midline of her body while she walked in the figure-8 pattern. Now, she is able to maintain midline and bilateral grasp for the duration of 4-5 rotations one way with minimal adult assistance. She is not yet able to maintain the grasp for the duration of the walk in the opposite direction.

Increase in expressive language. Client is primarily non-verbal; however, her expressive language skills have shown consistent growth from one week to the next.

Noticeable improvements include articulation, spontaneously sounds and sound blend combinations, as well as answering yes/no questions.

Client uses modified sign language to communicate her wants and needs. Her repertoire of signs continues to increase from week to week with the most significant gains related to the client's ability to multi-task. She is now using simple sign language paired with expressive vocalizations and direct eye contact. This is directly related to the brain's ability to do more than one activity all at the same time.

Increased midline and bilateral play skills. Initially the client used one hand during play. The other hand typically was left to hang by her side. It was difficult for this client to use both hands at the same time in the midline of her body, thus using both sides of her brain. The past three weeks immediately after walking on the Neuromat™, the client has spontaneously and independently used two hands during play. Specifically, she uses one hand to stabilize and the other one to activate. Examples include stacking graduated shapes, working a puzzle, coloring and using her IPAD.

Increased attention to task behavior. Prior to using the Neuromat™, this client attended to a preferred activity for 3-4 minutes before requiring a break. Typically, the break involved a sensory seeking activity. Currently, immediately following walking on the mat, this client has been able to maintain attention for 10-15 minutes without a break.

Marked improvement in overall behavior. Initially client D had numerous behavioral outbursts during therapy sessions. If her needs were not met immediately and on her terms, she would cry and scream for several minutes at a time, often unable to recover on her own. The last few weeks of therapy this client's behavior has not interfered with learning. Emotional outbursts have been controllable using a "first we do this, and then we do that" approach. The client has been able to regain control with a short hug from an adult and then able to transition back to the current activity.

Client E

Male; Age: 27 months

Needs: qualified at 23 months for Early Intervention Services based on cognitive delays, expressive and receptive language delays, fine motor and sensory integration disorder, emotional and coping delays. Client was diagnosed last week with ASD (Autism Spectrum Disorder)

Activity: Neuromat™ used one time per week for three weeks at the beginning of each developmental therapy session. Sessions were inconsistent due to child illness.

Development: Initially, the client was not able to tolerate walking a figure-8 pattern; nor was he able to tolerate being carried in a figure-8 pattern. So, for one week his mother put him in his push car and pushed him in a figure-8 pattern. Oct. 6, 2016, started using Neuromat™ in the home on a daily basis one time per day. Following one week, results are as listed:

Increased overall awareness. Improvements include looking when his name is called, making direct (but brief) eye contact and demonstrating shared enjoyment by smiling.

Decreased tantrums and crying episodes. Still several times per day, but parents report the tantrums are not as severe.

Tolerating being held when walking in a figure-8 pattern on the mat. Now able to tolerate 3-4 rotations each way.

Increased babbling during play.

Decreased self-stimulatory behavior.

Increased ability to transition activities with less disruptive behavior.

Developmental Therapist/Child Development Specialist
Female; Age: 55 years old

The Neuromat™ benefits the walker at any age. The present inventor uses the Neuromat™ with my clients several times per day 3-4 days per week. Personally, I have always suffered from motion sickness. This is no longer the case. I recently flew on an airplane and typically I would be affected by turbulence. The motion of the airplane would make me sick, which often resulted in a minor panic attack. This most recent trip I had no fight or flight response to tolerance.

The above description is not intended to limit the meaning of the words used in the following claims that define the invention. Persons of ordinary skill in the art will understand that a variety of other designs still falling within the scope of the following claims may be envisioned and used. It is contemplated that these additional examples, as well as future modifications in structure, function, or result to that disclosed here, will exist that are not substantial changes to what is claimed here, and that all such insubstantial changes in what is claimed are intended to be covered by the claims.

I claim:

1. A method for using a therapeutic tool for integrating motor, sensory and cognitive skills and progressively developing coordination and cognitive functioning, comprising the steps of:

providing a mat having an upper surface with a plurality of colored shapes collectively forming a figure-8 path with four different legs, and wherein each leg of the figure-8 path comprises different shapes, or shapes with different colors, and wherein each leg further comprises lights; and providing a programmable computer electronically connected to the mat, the computer being programmed to turn on and off the lights in predetermined sequences designed to prompt a user of the mat to progress along the figure-8 path.

2. The method of claim 1, wherein the computer saves progress of individual users on the mat, and plays a particular program, including light sequencing or music or both, targeted to individual users.

3. The method of claim 1, wherein use of the mat enables users to make substantial gains in one or more of the following areas: attention to task behavior; midline and bilateral play skills; articulation; use of expressive language; ambulatory skills; sensory integration skills; and attention.-to-task behavior.

4. The method of claim 1, wherein use of the tool enables users to make substantial gains in one or more of the following areas: attention to task behavior; midline and bilateral play skills; articulation; use of expressive language; ambulatory skills; sensory integration skills; and attention-to-task behavior.

5. The method of claim 1, wherein the computer saves progress of individual users on the mat, and plays a particular program, including involving light sequencing, targeted to facilitate therapeutic development of specific individual users.

6. The method of claim 1, wherein the computer saves progress of individual users on the mat, and plays a particular program, including specific music and light sequences, targeted to facilitate therapeutic development of specific individual users.

7. The method of claim 1, wherein the computer saves progress from sessions of specific individual users on the mat, and is programmed to plays a particular programs for the specific users, including specific light sequencing and music, targeted to facilitate therapeutic development of the specific users.

8. A therapeutic tool for integrating motor, sensory and cognitive skills and progressively developing coordination and cognitive functioning, comprising:

a mat having an upper surface with a plurality of colored shapes collectively forming a figure-8 path with four different legs, and wherein each leg of the figure-8 path comprises different shapes, or shapes with different colors, and wherein each leg further comprises lights; and a programmable computer electronically connected to the mat, for programming the lights targeted to work in a predetermined manner based on a history of past sessions on the mat by specific individual users of the mat, and designed to facilitate therapeutic development of the specific individual users, including to facilitate their induced progress along the figure-8 path.

* * * * *